US009986968B2

(12) United States Patent
Slak et al.

(10) Patent No.: US 9,986,968 B2
(45) Date of Patent: Jun. 5, 2018

(54) ULTRASONIC DEVICE FOR DENTAL IMPLANT NAVIGATION

(71) Applicant: UNIVERSITY OF WINDSOR, Windsor (CA)

(72) Inventors: Bartosz Slak, Windsor (CA); Emil Strumban, West Bloomfield, MI (US); Roman Maev, Windsor (CA)

(73) Assignee: University of Windsor, Windsor, Ontario (CA)

( * ) Notice: Subject to any disclaimer, the term of this patent is extended or adjusted under 35 U.S.C. 154(b) by 53 days.

(21) Appl. No.: 14/956,247

(22) Filed: Dec. 1, 2015

(65) Prior Publication Data

US 2016/0157815 A1 Jun. 9, 2016

Related U.S. Application Data

(60) Provisional application No. 62/088,511, filed on Dec. 5, 2014.

(51) Int. Cl.

| | | |
|---|---|---|
| *A61C 3/00* | (2006.01) | |
| *A61B 8/08* | (2006.01) | |
| *A61C 8/00* | (2006.01) | |
| *A61B 5/055* | (2006.01) | |
| *A61C 1/08* | (2006.01) | |
| *A61B 6/14* | (2006.01) | |
| *A61B 6/03* | (2006.01) | |
| *A61B 6/00* | (2006.01) | |
| *A61B 8/00* | (2006.01) | |

(52) U.S. Cl.
CPC ............ *A61B 8/0841* (2013.01); *A61B 5/055* (2013.01); *A61B 8/5261* (2013.01); *A61C 1/084* (2013.01); *A61C 8/0089* (2013.01); *A61B 6/032* (2013.01); *A61B 6/14* (2013.01); *A61B 6/4085* (2013.01); *A61B 8/4483* (2013.01); *A61B 8/463* (2013.01)

(58) Field of Classification Search
CPC ..... A61C 1/084; A61C 8/0089; A61B 8/0841; A61B 8/5261; A61B 5/055; A61B 6/032; A61B 6/14; A61B 6/4085; A61B 8/4483; A61B 8/463
See application file for complete search history.

(56) References Cited

U.S. PATENT DOCUMENTS

2007/0073136 A1* 3/2007 Metzger ............. A61B 17/1637
600/407
2011/0015521 A1* 1/2011 Faul ....................... A61B 34/20
600/426

(Continued)

OTHER PUBLICATIONS

G. Pellegrino et al., "A new navigation system for dental Implantology," Clinical Oral Implants Research, vol. 25, Issue S10, p. 297 (2014).

(Continued)

*Primary Examiner* — Heidi M Eide
(74) *Attorney, Agent, or Firm* — Womble Bond Dickinson (US) LLP

(57) ABSTRACT

The present invention providing a real-time positioning ultrasonic system that locates the dental implant drill bit relative to placed reference points or fiducial markers, and guides the drill entry point and angular trajectory, so that drilling is effected in the most optimum location in the jaw bone, as planned based on pre-surgery cone-beam computed tomography scans.

20 Claims, 4 Drawing Sheets

(56) References Cited

U.S. PATENT DOCUMENTS

2012/0015329 A1\* 1/2012 Gross ............... A61C 1/084
433/215
2015/0196369 A1\* 7/2015 Glossop ............ A61B 19/54
600/409

OTHER PUBLICATIONS

Satoshi Yamaguchi et al., "Intuitive Surgical Navigation System for Dental Implantology by Using Retinal Imaging Display," Chapter 13, pp. 301-317 (Aug. 2011).
George A. Mandelaris, et al., "Computer-guided implant dentistry for precise implant placement: combing specialized stereolithographically generated drilling guides and surgical implant instrumentation," The International Journal of Periodontics & Restorative Dentistry, vol. 30, No. 3, p. 275-281 (Jun. 2010).
"SIMPLANT® Guided Surgery—Delivering restorative driven implant treatment," Dentsply Implants, 12 pgs. (2014).
"SIMPLANT® Introducting SIMPLANT® 16—The key to unlocking digital potential," Dentsply Implants, 2 pgs. (2014).
"Prosthodontics Guided Surgery", University of Michigan—School of Dentistry, accessed at: http://www.dent.umich.edu/about-school/department/bms/prosthodontics/guided-surgery on Sep. 27, 2013, 1 page.

\* cited by examiner

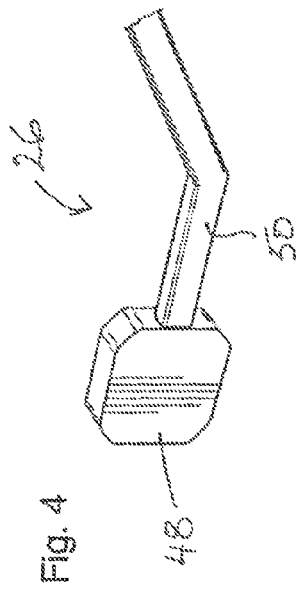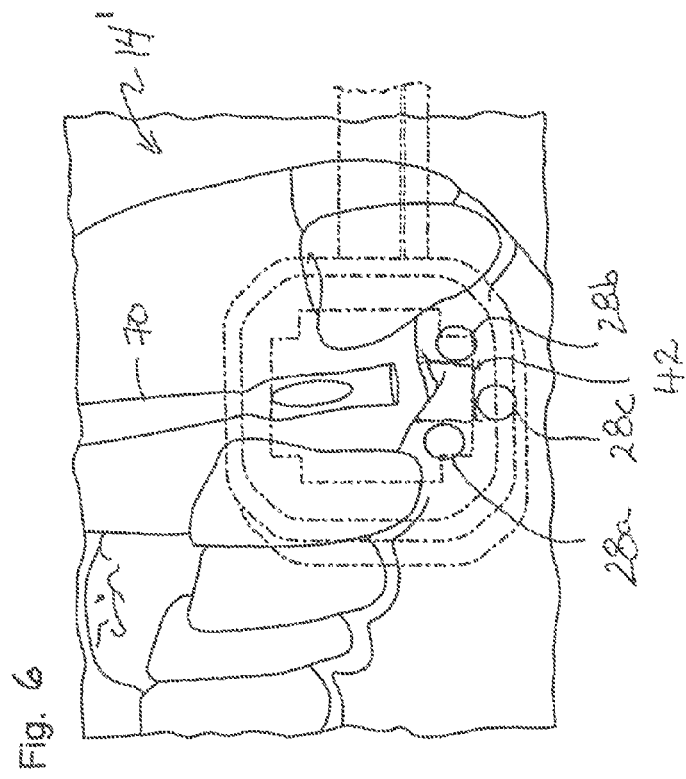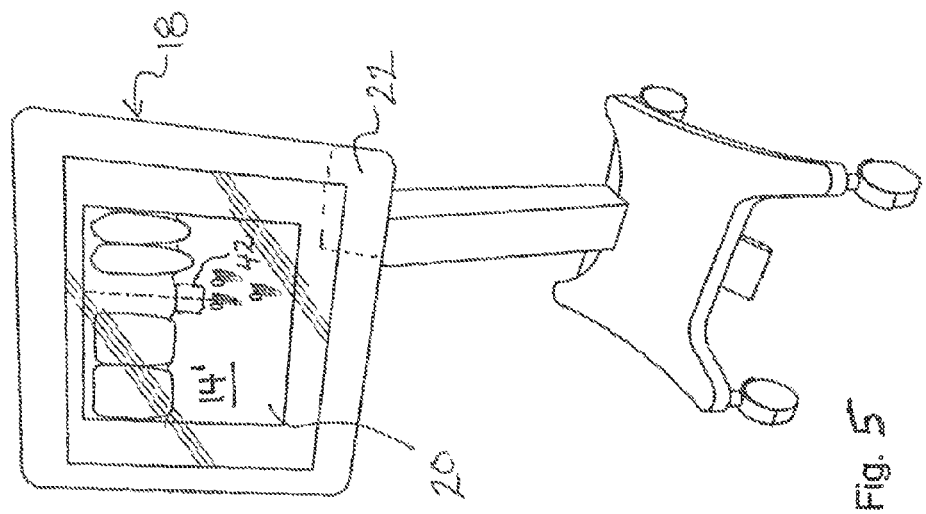

ULTRASONIC DEVICE FOR DENTAL IMPLANT NAVIGATION

RELATED APPLICATIONS

This application claims priority and the benefit of 35 USC § 119(e) to U.S. Provisional Patent Application Ser. No. 62/088,511, filed 5 Dec. 2014, the disclosure of which is incorporated herein by reference in its entirety.

SCOPE OF THE INVENTION

The present invention relates generally to the field of medical ultrasound. More particularly, the present invention relates to the field of ultrasound navigation systems intended for medical implants, and most preferably dental implantology. Preferably, the invention provides an ultrasonic-based system that provides a medical practitioner with a visual display which facilitates real-time guidance or location identification of an implant drill relative to an intended implant site in a patient's bone or tissue.

BACKGROUND OF THE INVENTION

Permanent dental implants have become a common method of replacing missing teeth. Prosthetic replacement teeth are supported by screws set into the jaw bone directly beneath the location where the tooth or teeth are missing and the replacement teeth are formed or mounted on the ends of the implant screw that protrudes above the gum line. The procedure of placing these screws into the jaw bone is done virtually blind by the dentist. As a result, there are many cases where implant screws are not properly placed, resulting in the failure of the dental implants and the removal and replacement of the implants with new implants or removable dental bridges anchored to adjacent teeth.

One important factor to the long term success of permanent dental implants resides in that the supporting screw is centered in the bone mass of the jaw at an angle directly under the load force that will be placed on the implant. The mechanical screw thread must be fully engaged with the jaw bone at a torque force that is less than the thread breakout force in the bone. The mechanical structure of implant screws is preferably such that it does not permit the implanted tooth to move or create pressure on the natural teeth next to the implants.

To ensure the pilot hole for the implant screw is properly placed, x-rays are taken, studied and reviewed to determine the best screw location and alignment. In most cases, the dental surgeon references the teeth he can see with x-rays or radiographs and positions the entry and alignment of the drill on visual observations. Conventional methods for dental implant placement typically involve freehand positioning based on subjective data such as visual examination with invasive bone structure exposure. Unfortunately, this method relies on specialist's skills and experience, extends the healing time and increases the risk of possible infection.

Custom fixtures that anchor on adjacent teeth with guide holes to properly align the drill have been attempted with limited success. Issues exist with the cost of fixture creation and the time required to place the fixture, and which unduly lengthen the time to the procedure, both in productivity for the doctor and comfort for the patient. As a result many dentists have reverted back to the freehand method, using the adjacent teeth as references to position and aligning the drill based on what was observed in the x-ray and accepting the failed procedures as the risk involved.

More sophisticated methods involve using cone-beam computed tomography (CBCT) data for implant placement planning, and CAD/CAM-based dental drill guide fabrication. The main utility of the guide is to transfer pretreatment planning information to the surgery site. The guide is usually made out of plastic and it is supported on residual or adjacent teeth, or in other cases attached with specially designed mini implants. Typically, such guides require the formation of metal sleeves which are immersed in plastic, and which act as jigs for positioning and depth control of the dental drill bit. Such system are personalized, entirely designed and fabricated based on pretreatment CBCT scans of the patient. Due to its complexity, involved risk and required accuracy, the guide fabrication is centralized and completed by professionals which increases the cost and considerably extending the restoration timeline.

SUMMARY OF THE INVENTION

Accordingly, to at least partially overcome some of the disadvantages associated with prior art devices, the present invention provides a system for facilitating the placement of implants, and in a preferred aspect, dental implants. The system incorporates a sensor which electronically communicates with a display, and which allows for substantially real-time imaging and display of an implant drill relative to a patient's particular biological area of interest, such as the intended area for implant placement.

The system operates in conjunction with a suitable imaging apparatus such as an x-ray apparatus, CBCT apparatus, magnetic resonance imaging apparatus (MRI) or the like, and which is operable to produce and store an output scanned image of the patient's intended implant area. The scanned image may be in a number of possible formats, including as a radiographic image, as well computer generated two-dimensional and/or three-dimensional images. The imaging apparatus may be located on site, or remotely, as for example at a hospital or clinic, with prepared output scanned image file being exported either electronically, or stored on portable storage media, such as a CD Rom, flash drive or other portable memory.

The system is provided with a processor having memory for receiving the output scanned image, and which electronically communications with a guidance system display. The system further includes a sensor assembly, and more preferably, an ultrasonic-based sensor assembly which operates in real-time to the processor for projection graphically an output on the data signals representing the position and/or orientation of a drill bit relative of the intended implant area. More preferably, the system operates in conjunction with one or more fiducial markers which are placed in the biological area of interest, and on the implant drill or other medical apparatus. Thus fiducial markers are positioned to allow for the correlation of the output scanned image produced by the imaging apparatus and the position of the drill bit and/or drill head detected by the ultrasonic sensor. The system may for example include software operable to automatically correlate the positioning of fiducial markers identified in the scanned output image with fiducial markers detected by the ultrasonic sensor. The system may therefore output on the display a visual representation of the drill and/or drill bit position in substantial real-time relative to the stored image. In this manner, the practioner may be able to view in substantially real-time the implant drill as it moves relative to the intended implant area.

In a most preferred construction, the fiducial markers are provided as part of a fiducial spatial coordinate system, in which three or more fiducial markers are fixed in position relative to the intended implant area, and in the case of a dental implant system in the patient's mouth. Alternately, one or more geometric or needle-shaped fiducial markers in the form of gold spheres may, for example, be used. Further, positional markers, and more preferably additional fiducial markers, are positioned on the drill or drill head in a predetermined orientation relative to a drill bit axis.

The applicant has appreciated that the present invention may thus provide an implant placement system, and preferably a dental implant drill guidance system which incorporates a drill and sensor arrangement which is cost effective, small and which is chosen to have a minimum effect on patient comfort. The present system further may work well with conventional implant placement methods and equipment, without adding to the overall length of the implantation procedure.

In another embodiment, the present invention provides a method and an apparatus for medical implant positioning, and preferably a dental implant positioning as part of placement procedure. Preferably, the present invention provides a real-time positioning ultrasonic system that locates the dental implant drill bit relative to one or more placed reference points or fiducial markers, and provides guidance as to the drill bit point and angular trajectory, so that drilling may proceed in the most optimum location in the jaw bone. More preferably, the intended implant position is pre-planned, based on a preselected orientation, imagery and/or pre-surgery MRI or cone-beam computed tomography scans. The pre-planned implant position may thus be modelled and stored in the processor memory for simultaneous projection to the display with the output scanned image.

The system display thus may graphically or visually locate and guide in real-time an implant drill relative to the optimum implant placement model. The system further may provide guidance as to the drill entry point, angular trajectory, and/or positional depth, such that drilling occurs in the most optimum location in bone, as determined from pre-procedure modelling and/or x-ray based calculations.

In another preferred embodiment, an ultrasonic system is proposed which tracks the drill bit location in real-time using designed fiducial markers, more preferably the markers are made of materials which create a strong contrast for both ultrasound and radiograph or x-ray images. Suitable fiduciary markers would therefore include those made from materials such as gold or amalgam. Other materials such as carbon, polymer and gutta-percha may, however, be used. In one use, one or more fixed reference markers or points are placed by a practitioner as part of a reference fiducial spatial coordinate system before CBCT scans are taken. The fixed fiducial markers preferably placed in close proximity to the intended implant placement or drilling area. After obtaining 3D x-ray data from the CBCT scan, the surgeon can pre-plan the implant surgery to select and model a preferred implant placement orientation using a virtual implant, as for example, by employing drag and drop tools in suitable implantology software. In this manner, it is possible to select the best implant screw or body placement trajectory for the particular host-patient's anatomy. The information about the optimal implant placement is then saved and sent to the guidance system display.

During the implant placement procedure, the ultrasonic probe is situated adjacent or in the mouth area in close proximity to the intended implantation site. The ultrasonic probe is preferably selected with a probe head which is sized to be comfortably received by the patient and contains a multi-element ultrasonic transducer array which is operable to form a space distributed ultrasonic beam. The probe head is preferably placed in a position selected to detect reflected ultrasonic signals from both the fixed reference fiducial markers, as well as fiducial markers on the drill or drill head at the same time. During one preferred mode of operation, the system processes received data representing the relative 3D positioning of the reference fiducial markers and fiducial marker position on the drill and calculates the current angulation and position of the drill bit relative to one or more of the reference fiducial markers previously imaged in the received pre-operative CBCT planning data. The system preferably enables the medical practioner or implantologist to observe on a monitor in real-time, drill bit position related to image intended implant area by generating and displaying graphically or by sensing a rendering of the drill bit position on the display. Optionally, the system may operate to provide visual and/or available warning informing about necessary corrections to correct drill bit penetration depth or to re-align the drill bit with the pre-planned trajectory. Preferably the system operates whereby in event that the sonic probe moves during the procedure, a displayed image may change, but the orientation of the drill relative to the reference points remains the same, and is continuously calculated by the matching algorithm.

Accordingly, in one aspect the present invention resides, a device for drill bit navigation in dental implant placement process, comprising: a tracking system which supplies information for guiding the drill bit during implant bed preparation by means of an output unit, said device producing a three-dimensional volume data set for the implant placing area, drill bit and fiducial markers by means of ultrasound imaging through an ultrasonic probe, said three-dimensional volume data set is used by said tracking system and exhibited by the output unit, wherein the output unit is a screen display, on which the implant placing area, drill bit, fiducial markers and a preplanned implant bed position are displayed in real-time during the implant bed preparation, and said screen display presents incorrect angulation of the drill bit when the preplanned positional path and the actual positional path of the drill bit deviate. More preferably, the device, produces an audible alarm should at any time the sonic probe not has three fiducial markers within the sonic probe vision area. The device may further have an image refresh rate greater than 30 times per second.

In another aspect, a dental implant placement system comprising: at least one fiducial marker adapted for placement in an intended implant area of a patient's mouth, said fiducial marker being detectable by both an ultrasonic sensor assembly and an imaging apparatus selected from the group consisting of an x-ray apparatus and a cone-beam computed tomography (CBCT) apparatus; an output assembly having a display electronically coupled to said ultrasonic sensor assembly and said imaging apparatus, the imaging apparatus being operable to produce and output on said display a three-dimensional image of said intended implant area; a drill assembly comprising: a drill bit actuable to form a bore in the patient's jaw at the intended implant area; and positional markers being detectable by said ultrasonic sensor assembly to provide an indication of an orientation of said drill bit in said patient's mouth, wherein the output assembly is operable to correlate the positional markers detected by said ultrasonic sensor assembly to said fiducial markers, and to output on said display a visual representation of said drill bit position relative to said three dimensional image.

In a further aspect, the present invention resides in An implant placement system comprising: at least one fiducial marker adapted for placement in an intended implant area of a patient's bone, said at least one fiducial marker being detectable by both an ultrasonic sensor assembly and an imaging apparatus selected from the group consisting of an x-ray apparatus, a magnetic resonance imaging apparatus and a cone-beam computed tomography (CBCT) apparatus; and an output assembly electronically coupled to said ultrasonic sensor assembly and said imaging apparatus, the output assembly including a display, and wherein the imaging apparatus is operable to produce and output to said display a visual image of said intended implant area, a drill assembly comprising: a drill bit actuable to form a bore in the patient's bone at the intended implant area; positional markers being detectable by said ultrasonic sensor assembly to provide an indication of an orientation of said drill bit relative to the intended implant area; and wherein in use, the output assembly is operable to correlate the positional markers detected by said ultrasonic sensor assembly to detected ones of said fiducial markers, and to display on said display a visual representation of said drill bit position relative to said visual image based on said correlation.

BRIEF DESCRIPTION OF THE DRAWINGS

FIGS. 3 and 4 illustrate schematically the ultrasonic probe used in the sensing of drill bit position shown in FIG. 2;

FIG. 5 illustrates schematically the guidance system processor and video display used in the system of FIG. 1; and FIG. 6 illustrates schematically a real-time output display of a visual graphic shown on the display video of FIG. 5, showing the relative movement of a sensed drill bit, relative to the patient's jaw bone during implant drilling.

DETAILED DESCRIPTION OF THE PREFERRED EMBODIMENTS

Figure 1:
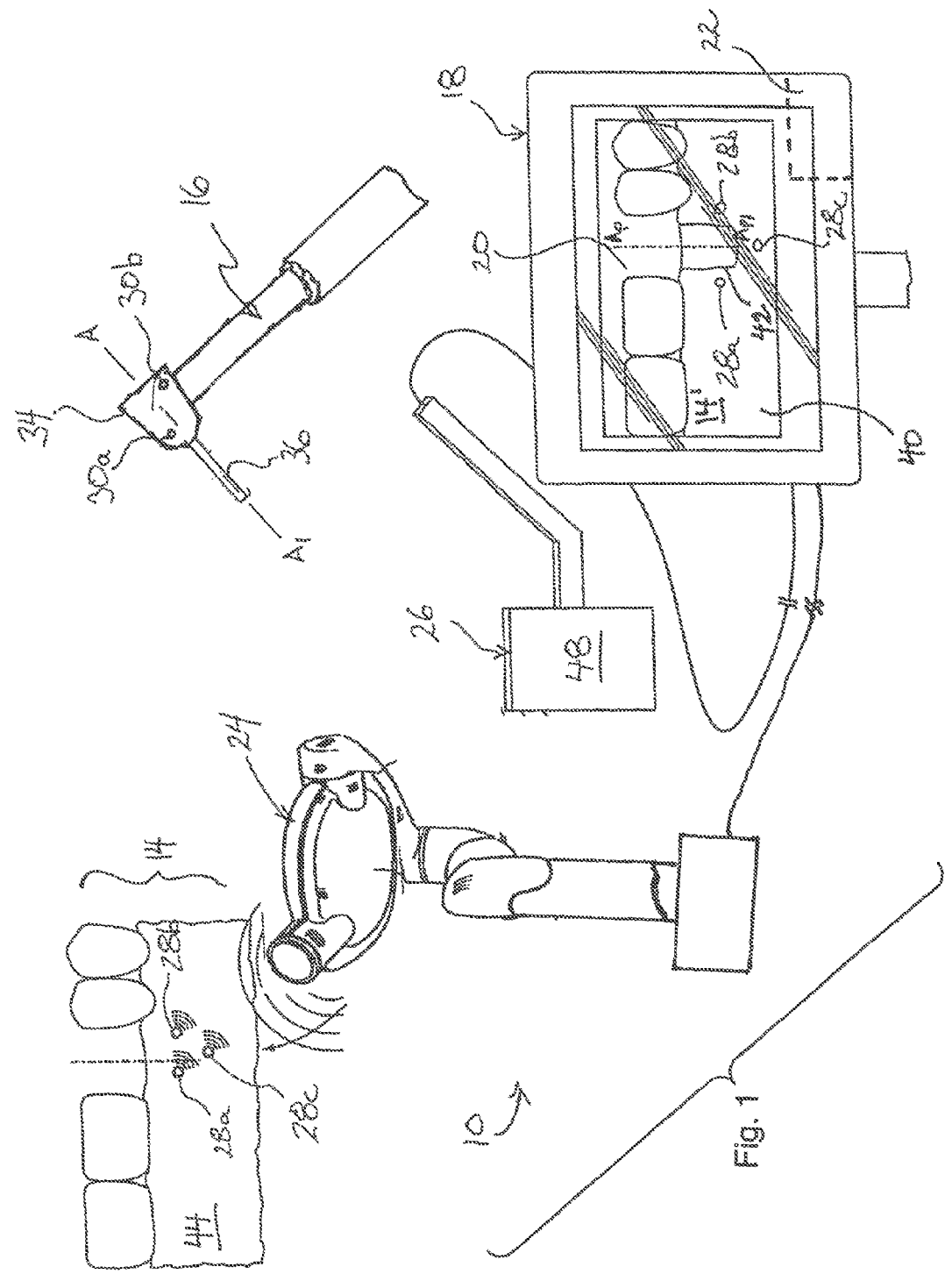
FIG. 1 shows a schematic view of dental implant placement system for use in positioning a dental implant in a human periodontium in accordance with a preferred embodiment of the invention.

Reference may be had to FIG. 1 which illustrates a dental implant placement system 10 in accordance with a preferred aspect of the invention. The implant placement system 10 is adapted to image and guide in real-time, the formation of desired implant bore 12 (FIG. 2) at an intended implant placement area 14 of patient's mouth. The implant placement system 10 includes a dental drill 16, an output display assembly or a signal processing unit 1 which includes a high resolution pixel display 20 and an internal processor 22 having storage memory and stored data management software, and which is electronically coupled to both a cone-beam computed tomography (CBCT) apparatus 24 and an ultrasonic sensor assembly 26. As will be described, the CBCT apparatus 24 and ultrasonic sensor assembly 26 each operate to detect fixed reference fiducial markers 28a,28b, 28c which are positioned on the patient's teeth or over the jaw bone 44 at or adjacent to the intended implant placement area 14. The ultrasonic sensor assembly 26 is further operable to detect and sense fiducial markers 30a,30b positioned on the dental drill 16 as part of a fiducial spatial coordinate system. Preferably, the fiducial markers 28,30 are spherical in shape with the diameter greater than the resolution of that used in the CBCT apparatus 24 and sensor assembly 26.

In FIG. 1, the fiducial markers 30a,30b are shown in a preferred configuration as being positioned in on the head 34 of the dental drill 16. Most preferably, the fiducial markers 30a,30b are pre-positioned in a known orientation relative to the drill chuck assembly such that in use of the implant placement system 10, when sensed, the fiducial markers 30a,30b provide information respecting the relative orientation of the drill bit axis $A-A_1$ relative to the implant placement area 14. Additional fiducial markers may also be provided along the length of the drill bit 36 or drill head 34. The system 10 may thus accurately monitor the forward progress of the drill bit 36 into the jaw bone 44 to ensure that the depth of the formed drill hole 12 is correct and in accordance with plan and technical requirements of the dental implant manufacturer.

FIG. 1 shows best the CBCT apparatus 24 as operable to generate and output to the signal processing unit 18 for viewing on the display 20 a scanned three-dimensional image 14' of the intended implant area 14 of the patient's mouth. Most preferably, the output three dimensional image 14' is stored in the memory of the internal processor 22 as computer generated graphic image. Preferably, the display 20 is provided with a touch screen 40 or other suitable user interface. The interface allows the medical practioner/dentist to input into the processor 22 and generate as part of the displayed image 14', a model 42 of an optimum implant bore hole. The model 42 is input so as to display as part of the image 14' indicia showing the optimum bore angular orientation and/or sized depth relative to the patient's jaw bone 44 to achieve the correct positioning of the desired implant (not shown) in a screw or press fit manner. The signal processing unit 18 is operable to output to the display 20 a visual image of the implant bore model 42 concurrently as part of the output three-dimensional image 14', illustrating schematically the optimum bore placement relative to the patient's jaw bone 44. More preferably, the processing unit 18 further generates and displays with the image 14' a graphic or indicia representative of the drill bit 36 placement at the intended placement area 14 as it moves relative to the jaw bone 44.

Figure 2:
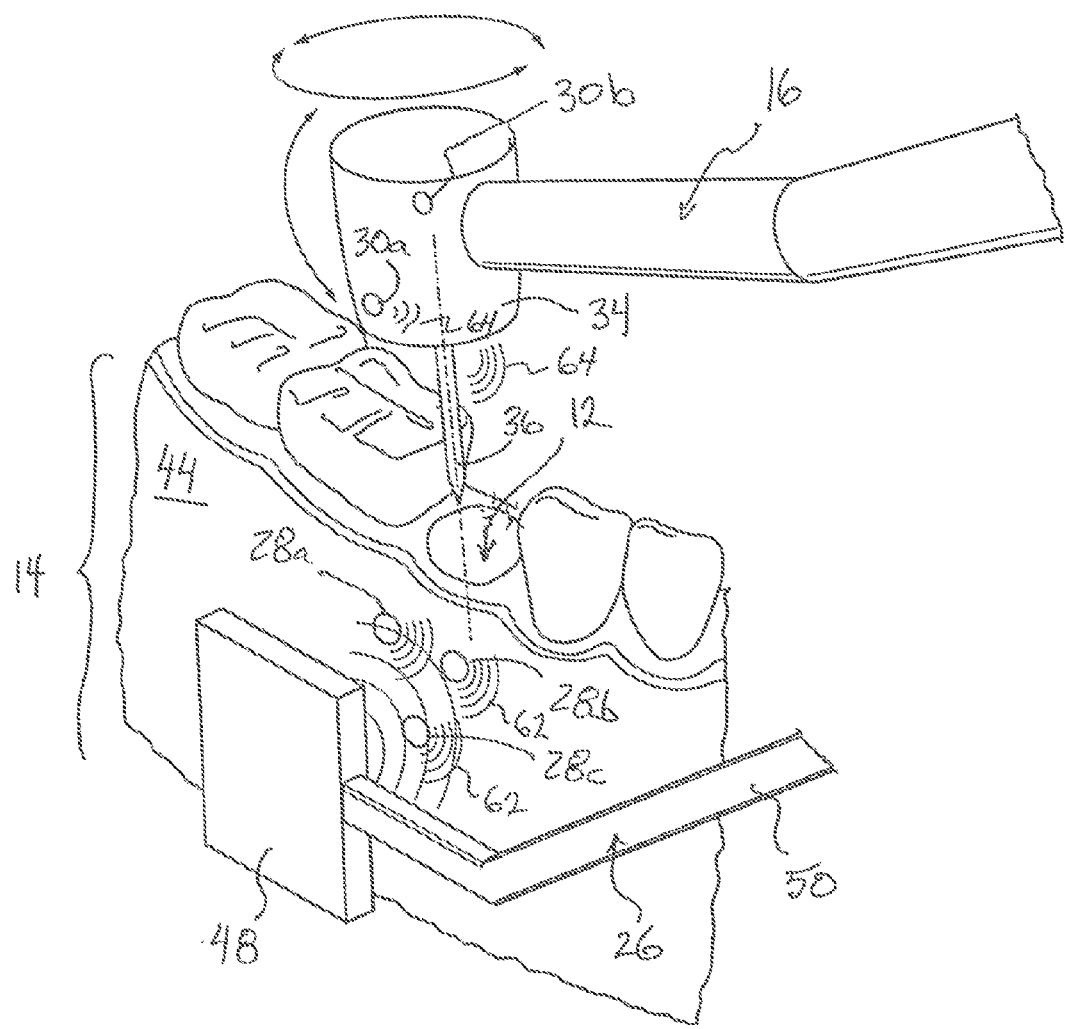
FIG. 2 is a partial perspective view showing the operation of an ultrasonic probe of the system of FIG. 1, in sensing the position of a drill bit position during drilling operations.
Figure 3:
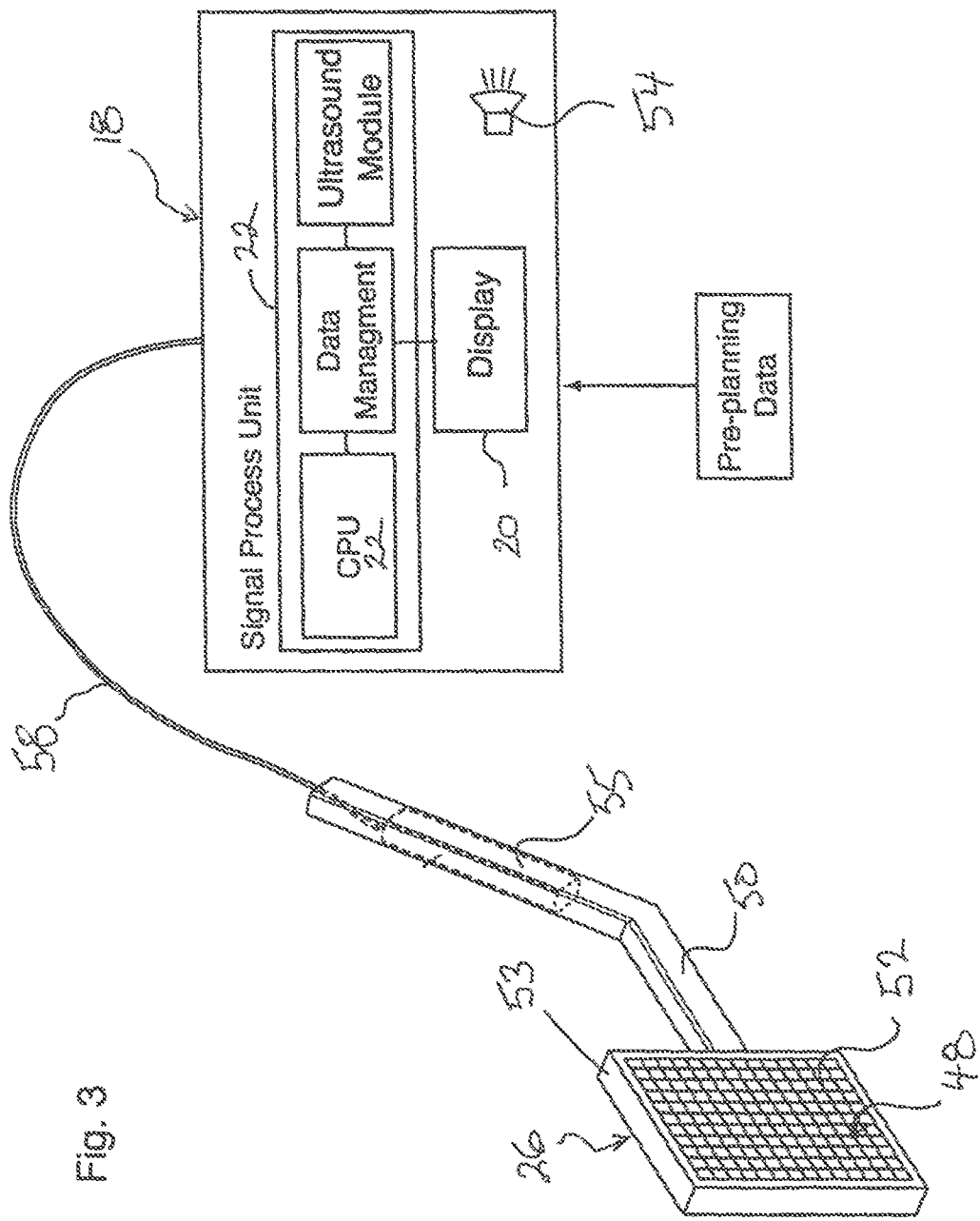

As shown best in FIGS. 2 to 4, the ultrasonic sensor assembly 26 includes an ultrasonic sensor head 48 which is mounted on a positioning arm 50. The sensor head 48 is sized to allow for its positioning within the patient's mouth and adjacent to the intended placement area 14, so as to be operable to sense simultaneously both the fixed reference fiducial markers 28a,28b,28c, as well as the fiducial markers 30a,30b mounted on the drill 16. The sensor head 48 is selected to sense and transmit to the signal processing unit 18 data signals representative of sensed relative positioning of the fiducial markers 28a,28b,28c,30a,30b, thus providing data from which the relative drill bit 36/jaw bone 44 position may be determined. Fiducial markers 28a, 28b, and 28c provide reference points to merge the various image data to one common reference frame.

Furthermore FIG. 3, shows the ultrasonic sensor head 48 as preferably includes a multi-element transducer matrix 52 within a biocompatible enclosure 53. The ultrasonic sensor assembly 26 may also have a built-in electronic control block 55 responsible for direct transducer control, and which is located in the positioning arm 50. The electronic block 55 is connected to the signal processing unit 18 by a suitable digital cable 58. The stored data management software in the processor 22 electronically communicates with the array transducer control block 55 to create and manipulate emitted ultrasonic beams.

The ultrasonic waves reflected by the fiducial markers 30a,30b which are placed at known locations on the drill head 34 are received by transducer matrix 52 and connected to data signals. The signals are sent to the processor 22 that uses the known relationship between 30a, 30b and drill bit 36 to calculate the axis A-A₁ of vertical drill bit 36 then uses common fiducial markers 28a, 28d, 28c, alignment to position (depth and angle of drilling) relative to the jaw bone 44. In particular, the signals 62,64 reflected respectively from both sets of the fiducial markers 28a,28b,28c,30a,30h are acquired by the probe head 48, converted to electrical signals, and sent to processor 22 for further processing. Concurrently the sensed position of the reference fiducial markers 28a,28b,28c detected by the sensor assembly 26 is used to correlate the sensed drill 16 position with the input image 14'. Based on the detected signals 62,64, a secondary graphic image 70 representative of the drill bits 36 is preferably generated, and which is representative of the drill position and orientation. The secondary graphic image 70 is displayed on the display 20, overlain on the 3D image 14'. The secondary graphic image 70 is preferably created and analyzed by extracting features and aligning reference points between the two modalities data, namely, the reference data of the fixed fiducial markers 28a,28b,28c and the second fiducial markers 30a,30b. The processor 22 thus operates to accurately merge the input 3D virtual model image 14' based on the CBCT scan with live ultrasonic generated images.

In use of the system 10, a dental surgeon may place three or more spherical reference fiducial markers 28a,28b,28c semi-permanently, as for example with adhesive onto the patient's gum tissue and/or teeth, at the intended implant area 14 where the surgery is to take place. The intended placement area 14 is then imaged, by the CBCT apparatus 24 to generate and output the scanned image 14' to the signal processing unit 18. The generated x-ray images are preferably then stored in the signal processing unit 18 processor memory and illustrated on the display 20 where the surgeon analyses the site conditions, and determines the optimum position and angle for the implant screw(s). Most preferably, the optimum implant screw center line(s) and depth is calculated and plotted directly as part of the displayed image 14' using the touch screen 40.

Following initial scanning by the CBCT apparatus 24 and the determination and input of the model 42 into the processor 22, the ultrasonic assembly 26 and dental drill 32 are then used in conjunction with the displayed 3D image 14' to form the desired bore 12 having the optimum configuration.

The implant placement system 10 is operated for optimum drill guidance in real-time. As shown best in FIG. 2, the ultrasonic sensor assembly 26 is used concurrently with the operation of the dental drill 16 to accurately locate the point of entry and then precisely align the implant drill bit 36 with the predetermined optimum trajectory of the modelled bore hole 42 to form the bore 12 in the patient's jaw bone 44. In use, the positioned fiducial markers 28a,28b,28c,30a,30b that are visible in the real-time ultrasonic image to guide the drill bit 36.

The patient is thus prepared for surgery and the ultrasonic sensor head 48 is placed in the intended implant placement area 14 of the patient's mouth, in an orientation directed at the intended implant location. Optionally, the ultrasonic probe head 48 may be coupled with the implant placement area 14 by means of water or gel-based agent. Preferably, the system display 20 operates to output concurrently two images on the screen 40: one based on the initial scanned x-ray image 14', with the plotted centerline of modelled bone 42 locations; and the second being the generated secondary image 70 representative of the actual drill bit 36 position, as determined a live feed from the ultrasonic sensor head 40 and the relative drill 16.

Referring to FIGS. 2 and 6 there is shown the human periodontium or, jaw bone 44 with an implant placement location area 14 together with adjacent teeth. The dental drill 16 with mounted drill bit 36 is positionable over the intended implant site. The ultrasonic probe head 48 is located in front of the intended implant site 14, and operates to generate a beam of ultrasound propagating towards the prepositioned fiducial markers 28a,28b,28c,30a,30b. During drilling operation, the real-time position of the drill bit 36 is relative to the jaw bone 44, is thus sensed, and output graphically as the secondary graphic image 70 on the display 20 superimposed with the image 14. If the angulation and position of the drill bit 36 deviates from a planned axis $A_P$-$A_{P1}$ the system 10 will inform the surgeon on either the display 20 and/or as well as acoustically using a built-in speaker 54 (FIG. 3). By pre-selecting degrees of freedom of drill 16 movement (FIG. 3) it is possible to allow the practitioner to readjust the drill bit 36 trajectory as necessary, while the ultrasonic sensor assembly 26 continuously operates to obtain updated images and calculate current drill bit 36 position.

The placed reference fiducial markers 28a,28b,28c further preferably appear in both displayed images. As a result, the surgeon may electronically align the reference fiducial markers 28 on the x-ray image with those of the live ultrasonic feed. Once this alignment (or near alignment) has been achieved, a software function may be used to electronically lock the input x-ray image 14' to the live ultrasonic feed image by digitally keeping the reference fiducial markers 28 aligned image-to-image, creating a single scale and reference frame for the two images being viewed one on top of the other as one continuous image. While the drill bit 36 is advanced into the bone 44, the area 14 is preferably continuously scanned and a detected ultrasonic image showing drill bit 36 placement appears on screen in real-time. By aligning the drill bit 36 so that its image 70 is moved into alignment with the preselected center line trajectory plotted or modelled on the screen 20, the practitioner may maintain optimum desired drill bit 36 alignment, correcting as required based on the planned line of trajectory.

In the event that the ultrasonic sensor assembly 26 moves during the procedure, the displayed image 14' may change slightly as the images stay synchronized. The alignment of the drill bit 36 to the reference fiducial markers 28 and/or modelled image 42 will, however, maintain the desired reference basis.

In an alternate embodiment, the drill bit 36 may be provided with a number of markers around the shank to ultrasonically visualize the drill bit orientation, length, diameter, and depth. In another possible embodiment, dental implant drill 16 may be provided with ring feature near the chucked end of the drill head 34. The ring feature is chosen from a known distance from the tip of the drill and is visible in the real-time as part of the generated ultrasonic image. When the drill bit 36 is at the proper depth in the formed bore 12, the depth ring will be at a predetermined position along the drill angle trajectory, and may be sensed by the system 10 to provide the surgeon both a visual and audible signal to stop drilling.

The system 10 of the present invention preferably is programmed to include a number of non-limiting operational features, and which may for example include:
1. Dental implant drill guidance programme instructions that use x-ray images; developed procedure plan data; and live ultrasonic imaging layered and aligned with placed marker spheres to provide critical drill entry, alignment, and drill depth information in real-time to the surgeon for the optimum placement of the dental implant mounting screw(s).
2. Software and analytics which, from a limited number of patient x-rays or, extrapolate data to provide adequate 3D interpolation for the development of a procedure plan and drill guidance measurements for entry location; 3D drilling angle; and drilling depth.
3. Software which is operable to accurately merge data from x-ray; procedure development drawings; and real-time ultrasonic imaging into one image using marker spheres to assure the accuracy of this alignment. Further, once aligned imaging coordination software maintains the alignment and merger of these images in real-time by actively keeping the marker spheres on all images aligned with, the marker spheres on the real-time sonic image. In this way the sonic probe may be moved and re-orientated for a better viewing angle and image without having to rebuild the image merger.
4. A CMUT based multi micro transducer probe head 48 which is provided for better imaging; higher resolution; with little or no heat generation allowing for extended real-time imaging without the need to cool the probe to accommodate patient comfort and safety.
5. The system 10 may operate to capture a real image with the ultrasonic probe head 48 and generates a virtual image of the tissue and bone from x-ray data for areas not visible to the ultrasonic probe.
6. Use of fiducial markers 28,30 allows for the alignment of produced images from several sources; as well as 2D images virtually transformed into 3D images to provide full data to the surgeon.
7. Use of spherical fiducial markers to assure image scaling is coordinated with the scale of the real-time ultrasonic image.

It is recognized that in a preferred embodiment, the system 10 contemplates the construction of a three-dimensional virtual image 14' built from multiple 2D scan or x-ray images, whereby
1. The surgeon views each x-ray on the screen and assigns a unique identifier to each reference fiducial marker 28 on the first image.
2. The surgeon then assigns the same identifier to the corresponding marker 28 in every x-ray image.
3. The system then scales and overlays all of the fiducial markers as per identifier, thus making each x-ray a cross section through a virtual 3D image as per the alignment of that x-ray.
4. The system processing software is configured to allow the system to use this information to create a virtual 3D image 14' over these sections.
5. The surgeon can now use the generated virtual 3D image 14' upon which to plot and develop his implant screw placement In a possible operating mode, the virtual image 14' is merged with the real-time ultrasonic image. On a first ultrasonic image appearing on a display screen 40, the processor 32 or surgeon again assigns the same identifiers to the fiducial markers 28 in the image, as was done for the fiducial markers in the virtual image, and then aligns both images on the display screen 40. Once alignment has been completed, the system 10 electronically locks the x-ray based model 14' in constant re-alignment with the real-time ultrasonic image. As a result, even if the ultrasonic probe head 48 is moved, the images will remain properly aligned and to scale with the real-time ultrasonic image.

While the detailed description describes the implant placement system 10 as used in the positioning of a dental implant in a patient's jaw hone 44, the invention is not so limited. It is to be appreciated that the system 10 may equally be used in the positioning of other types of implants in other loci in patient's bone and/or soft tissues.

Similarly, while the detailed description describes the ultrasonic sensor assembly 26 as sensing and indicating the orientation of a drill bit relative to an intended installation location, the system may also be used to detect and display in real-time, the relative positioning of a variety of medical tours and/or appliances relative to a selected biological area of interest.

While the detailed description describes the fiducial spatial coordinate system as including three reference fiducial markers 28a,28b,28c and two fiducial markers 30a,30b, the invention is not so limited. It is to be appreciated that fewer or greater numbers of fiducial markers may be provided, depending upon the imaging and sensor capabilities.

Although FIG. 1 illustrates the CBCT apparatus 24 as being electronically connected directly to the signal processing unit 18, the invention is not so limited. It is to be appreciated that in a more economical construction, the CBCT apparatus 24 could be provided at a remote location and where for example, a single CBCT apparatus 24 may be used to produce and transmit scanned images of different patient implant placement areas for use on separate signal processing units 18 and displays 20 at different locations.

Although the delated description describes and illustrates various preferred embodiments, the invention is not so limited. Many variations and modifications will now occur to persons skilled in the art. For a definition of the invention, reference may be had to the appended claims.

We claim:
1. A dental implant placement system comprising:
at least one fiducial marker adapted for placement in an intended implant area of a patient's mouth; an ultrasonic sensor assembly, said ultrasonic assembly comprising an ultrasonic sensor sized for positioning in said patient's mouth generally adjacent said intended implant area;
an imaging apparatus selected from the group consisting of an x-ray apparatus and a cone-beam computed tomography (CBCT) apparatus;
said fiducial marker being detectable by both the ultrasonic sensor and the imaging apparatus;
an output assembly having a display electronically coupled to said ultrasonic sensor assembly and said imaging apparatus, the imaging apparatus being operable to produce and output on said display a three-dimensional image of said intended implant area;
a drill assembly comprising:
a drill bit actuable to form a bore in the patient's jaw at the intended implant area; and
positional markers being detectable by said ultrasonic sensor to provide an indication of an orientation of said drill bit in said patient's mouth, wherein the output assembly is operable to correlate the positional markers detected by said ultrasonic sensor to said fiducial markers, and to output on said display a visual representation of said drill bit position relative to said three dimensional image.
2. The implant placement system as claimed in claim 1, wherein said output assembly is operable to receive data representative of a modelled preferred implant placement orientation at said intended implant area, and to output on said display with said three-dimensional image placement orientation data representative of said preferred implant placement orientation.

3. The implant placement system as claimed in claim 2, wherein said data representative of said preferred implant placement orientation comprises a visual representation of a preferred bore position and depth relative to said patent's jaw.

4. The implant placement system as claimed in claim 3, wherein said visual representation is superimposed on said three dimensional image.

5. The implant placement system as claimed in claim 1, wherein the drill assembly comprises a dental drill having a drill head, said drill bit being mounted in said drill head for selective journaling in rotation about a drill axis, said positional markers comprising a plurality of markers mounted to said dental drill relative to said drill axis.

6. The implant placement system as claimed in claim 1, wherein said fiducial markers are imageable by at least one of said ultrasonic sensor assembly and said imaging apparatus for output on said display with said output three-dimensional image.

7. The implant placement system as claimed in claim 1, wherein said output assembly is operable to effect correlation of said positional markers and said fiducial markers substantially in real-time.

8. The implant placement system as claimed in claim 1, wherein the output assembly is operable to display with said three-dimensional image a modelled bore image, said modelled bore image representative of an optimum bore orientation, depth and/or configuration sized to receive a dental implant seated therein in a screw-fit, press-fit or compression-fit manner.

9. The implant placement system of claim 1, wherein the output assembly includes a processor having data management software stored thereon, said data management software being operable in substantially real-time to correlate fiducial marker position detected by said ultrasonic sensor assembly with a fiducial marker position detected by said imaging apparatus.

10. An implant placement system comprising:
at least one fiducial marker adapted for placement in an intended implant area of a patient's mouth;
an ultrasonic sensor assembly, the said ultrasonic sensor assembly comprising an ultrasonic sensor for positioning adjacent said intended implant area in said patient's mouth;
an imaging apparatus selected from the group consisting of an x-ray apparatus, a magnetic resonance imaging apparatus and a cone-beam computed tomography (CBCT) apparatus;
said at least one fiducial marker being detectable by both the ultrasonic sensor and the imaging apparatus; and
an output assembly electronically coupled to said ultrasonic sensor assembly and said imaging apparatus, the output assembly including a display, and wherein the imaging apparatus is operable to produce and output to said display a three-dimensional visual image of said intended implant area,
a drill assembly comprising:
a drill bit actuable to form a bore in the patient's bone at the intended implant area;
positional markers being detectable by said ultrasonic sensor to provide the position and orientation of said drill bit relative to the intended implant area; and
wherein in use, the output assembly is operable to correlate the positional markers detected by said ultrasonic sensor to detected ones of said fiducial markers, and to display on said display a visual representation of said drill bit position relative to said visual image based on said correlation.

11. The implant placement system as claimed in claim 10, wherein said output assembly is operable to receive data representative of a modelled preferred implant placement orientation at said intended implant area, and to output on said display with said visual image, placement orientation data representative of said preferred implant placement orientation.

12. The implant placement system as claimed in claim 11, wherein said data representative of said preferred implant placement orientation comprises a visual representation of a preferred bore placement and depth relative to said patent's bone.

13. The implant placement system as claimed in claim 12, wherein the implant comprises a dental implant and wherein the visual representation of a preferred bore placement and depth comprise a virtual computer generated bore sized to receive the dental implant seated therein in a screw-fit, press-fit or compression-fit manner.

14. The implant placement system of claim 12, wherein the output assembly includes a processor having data management software stored thereon, said data management software being operable in substantially real-time to correlate fiducial marker position detected by said ultrasonic sensor assembly with a fiducial marker position detected by said imaging apparatus.

15. The implant placement system as claimed in claim 10, wherein the intended implant area is an area of a patient's jaw bone, and wherein the drill assembly comprises a dental drill having a drill head, said drill bit being mounted in said drill head for selective journaling in rotation about a drill bit axis, said positional markers comprising a plurality of fiducial markers mounted to drill relative to said drill bit axis.

16. The implant placement system as claimed in claim 10, wherein said fiducial markers are imageable by at least one of said ultrasonic sensor assembly and said imaging apparatus for output on said display with said output three-dimensional image.

17. The implant placement system as claimed in claim 10, wherein said output assembly is operable to effect a correlation of said positional markers with said fiducial markers substantially in real-time.

18. A dental implant placement system comprising:
a plurality of fiducial markers adapted for placement in an intended implant area within a patient's mouth;
an ultrasonic sensor assembly, said ultrasonic assembly comprising an ultrasonic sensor sized for positioning in said patient's mouth generally adjacent said intended implant area;
an imaging apparatus selected from the group consisting of an x-ray apparatus and a cone-beam computed tomography (CBCT) apparatus;
said fiducial markers being detectable by both the ultrasonic sensor and the imaging apparatus;
an output assembly having a display electronically coupled to said ultrasonic sensor assembly and said imaging apparatus, the imaging apparatus being operable to produce and output on said display a three-dimensional image of said intended implant area;
a drill assembly comprising:
a drill head mounting a drill bit actuable to form a bore in the patient's jaw at the intended implant area; and
said ultrasonic sensor being operable to detect said drill head to provide an indication of an orientation of said drill bit in said patient's mouth, wherein the output assembly is operable to correlate the position of the drill head detected by said ultrasonic sensor to said fiducial markers, and to output on said display a visual representation of said drill bit position relative to said three dimensional image.

19. The implant placement system as claimed in claim 18, wherein the output assembly is operable to display with said three-dimensional image a modelled bore image, said modelled bore image representative of an optimum bore orientation, depth and/or configuration sized to receive a dental implant seated therein in a screw-fit, press-fit or compression-fit manner.

20. The implant placement system of claim 19, wherein the output assembly includes a processor having data management software stored thereon, said data management software being operable in substantially real-time to correlate fiducial marker position detected by said ultrasonic sensor assembly with a fiducial marker position detected by said imaging apparatus.

* * * * *